United States Patent
Heaton et al.

(10) Patent No.: US 6,600,315 B1
(45) Date of Patent: Jul. 29, 2003

(54) METHOD FOR IMPROVING RESOLUTION OF NUCLEAR MAGNETIC RESONANCE MEASUREMENTS BY COMBINING LOW RESOLUTION HIGH ACCURACY MEASUREMENTS WITH HIGH RESOLUTION LOW ACCURACY MEASUREMENTS

(75) Inventors: Nicholas J. Heaton, Houston, TX (US); Charles Flaum, Ridgefield, CT (US); Chanh Cao Minh, Katy, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 09/681,061

(22) Filed: Dec. 14, 2000

Related U.S. Application Data

(60) Provisional application No. 60/186,877, filed on Mar. 3, 2000.

(51) Int. Cl.$^7$ ............................................. C01V 3/00
(52) U.S. Cl. ........................................................ 324/303
(58) Field of Search ............................................ 324/303

(56) References Cited

U.S. PATENT DOCUMENTS

| | | | | | |
|---|---|---|---|---|---|
| 5,363,041 | A | * | 11/1994 | Sezginer | 324/300 |
| 5,387,865 | A | * | 2/1995 | Jerosch-Herold et al. | 324/303 |
| 5,419,405 | A | * | 5/1995 | Patton | 175/27 |
| 5,486,762 | A | * | 1/1996 | Freedman et al. | 324/303 |
| 5,680,043 | A | * | 10/1997 | Hurlimann et al. | 324/303 |
| 5,936,405 | A | * | 8/1999 | Prammer et al. | 324/303 |
| 6,005,389 | A | * | 12/1999 | Prammer | 324/303 |
| 6,049,205 | A | * | 4/2000 | Taicher et al. | 324/303 |
| 6,069,477 | A | * | 5/2000 | Chen et al. | 324/303 |
| 6,115,671 | A | * | 9/2000 | Fordham et al. | 702/8 |
| 6,140,817 | A | * | 10/2000 | Flaum et al. | 324/300 |
| 6,204,663 | B1 | * | 3/2001 | Prammer | 324/303 |
| 6,242,912 | B1 | * | 6/2001 | Prammer et al. | 324/303 |
| 6,253,155 | B1 | * | 6/2001 | Hagiwara | 702/9 |
| 6,255,818 | B1 | * | 7/2001 | Heaton et al. | 324/303 |
| 6,255,819 | B1 | * | 7/2001 | Day et al. | 324/300 |
| 6,377,042 | B1 | * | 4/2002 | Menger et al. | 324/303 |

* cited by examiner

Primary Examiner—Edward Lefkowitz
Assistant Examiner—Dixomara Vargas
(74) Attorney, Agent, or Firm—Kevin P. McEnaney; Brigitte L. Jeffery

(57) ABSTRACT

A method that is usable with an NMR measurement apparatus includes averaging first spin echo trains acquired from different regions of a sample to form a second spin echo train. The first spin echo trains are used to produce a first estimate of a property of the sample, and the first estimate has a first resolution and a first accuracy. The second spin echo train is used to produce a second estimate of the property, and the second estimate has a second resolution that is lower than the first resolution and a second accuracy that is higher than the first accuracy. The first and second estimates are combined to produce a third estimate of the property. The third estimate has a third resolution near the first resolution of the first estimate and a third accuracy near the second accuracy of the second estimate.

86 Claims, 7 Drawing Sheets

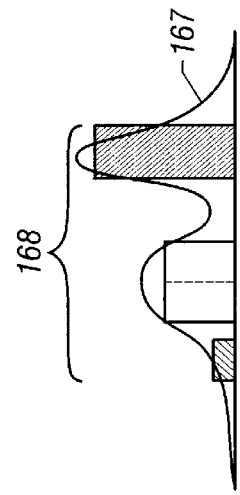
FIG. 8
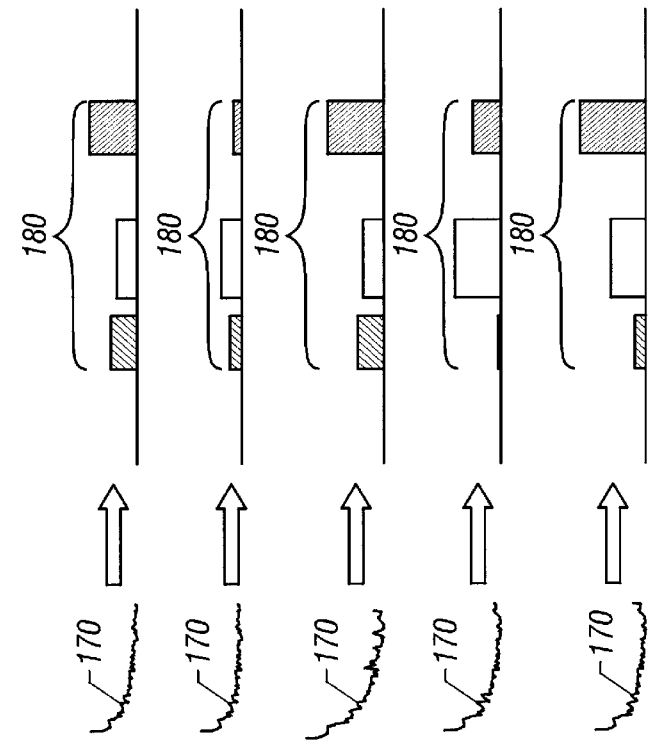
FIG. 9
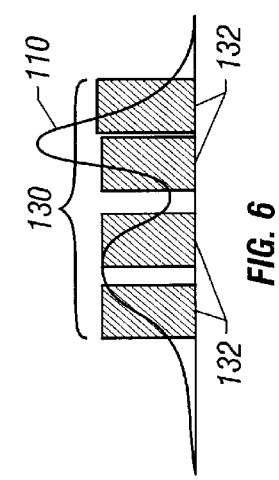
FIG. 5
FIG. 6
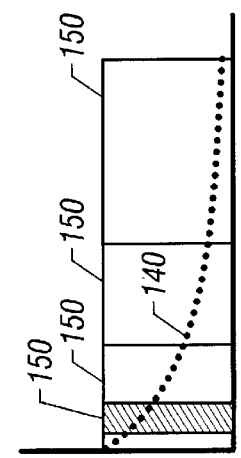
FIG. 7

METHOD FOR IMPROVING RESOLUTION OF NUCLEAR MAGNETIC RESONANCE MEASUREMENTS BY COMBINING LOW RESOLUTION HIGH ACCURACY MEASUREMENTS WITH HIGH RESOLUTION LOW ACCURACY MEASUREMENTS

CROSS REFERENCE TO RELATED APPLICATIONS

Under 35 U.S.C. §119, this application claims the benefit of U.S. Provisional Patent Application Ser. No. 60/186,877, filed on Mar. 3, 2000.

BACKGROUND OF INVENTION

This invention generally relates to a technique to achieve high resolution measurements of petrophysical properties, and more particularly, the invention relates to a technique to generate accurate and high resolution estimates of petrophysical properties by the use of alpha processing.

Nuclear magnetic resonance (NMR) measurements typically are performed to investigate properties of a sample. For example, an NMR wireline or logging while drilling (LWD) downhole tool may be used to measure petrophysical properties that are associated with downhole formations. In this manner, a typical NMR tool may, for example, provide a lithology-independent measurement of the porosity of a particular formation by determining the total amount of hydrogen present in fluids of the formation. Equally important, the NMR tool may also provide measurements that indicate the dynamic properties and environment of the fluids, as these factors may be related to petrophysically important parameters. For example, the NMR measurements may provide permeability and viscosity information that is difficult or impossible to derive from other conventional logging arrangements. Thus, it is the capacity of the NMR tool to perform these measurements that makes it particularly attractive versus other types of downhole tools.

Typical NMR logging tools include a magnet that is used to polarize hydrogen nuclei (protons) in the formation and a transmitter coil, or antenna, that emits radio frequency (RF) pulses. A receiver antenna may measure the response (indicated by received spin echo signals) of the polarized hydrogen to the transmitted pulses. Quite often, the transmitter and receiver antennae are combined into a single transmitter/receiver antenna.

There are several experimental parameters that may be adjusted according to the objectives of the NMR measurement and expected properties of the formation fluids. However, the NMR techniques employed in current NMR tools typically involve some variant of a basic two step sequence that includes a polarization period followed by an acquisition sequence.

During the polarization period (often referred to as a wait time) the protons in the formation polarize in the direction of a static magnetic field (called $B_o$) that is established by a permanent magnet (of the NMR tool). The growth of nuclear magnetization M(t) (i.e., the growth of the polarization) is characterized by the "longitudinal relaxation time" (called T1) of the fluid and its maximum value (called $M_0$), as described by the following equation:

$$M(t) = M_0\left(1 - e^{-\frac{t}{T_1}}\right)$$

The duration of the polarization period may be specified by the operator (conducting the measurement) and includes the time between the end of one acquisition sequence and the beginning of the next. For a moving tool, the effective polarization period also depends on tool dimensions and logging speed.

Referring to FIG. 1, as an example, a sample (in the volume under investigation) may initially have a longitudinal magnetization $M_Z$ 10 of approximately zero. The zero magnetization may be attributable to a preceding acquisition sequence, for example. However, the magnetization $M_Z$ 10 (under the influence of the $B_0$ field) increases to a magnetization level (called $M(t_w(1))$) after a polarization time $t_w(1)$ after zero magnetization. As shown, after a longer polarization time $t_w(2)$ from zero magnetization, the $M_Z$ magnetization 10 increases to an $M(t_w(2))$ level.

An acquisition sequence begins after the polarization period. For example, an acquisition sequence may begin at time $t_w(1)$, a time at which the magnetization $M_Z$ 10 is at the $M(t_w(1))$ level. At this time, RF pulses are transmitted from a transmitter antenna of the tool. The pulses, in turn, produce a train of spin echo signals 16, and the initial amplitudes of the spin echo signals 16 indicate a point on the magnetization $M_Z$ 10 curve, such as the $M(t_w(1))$ level, for example. Therefore, by conducting several measurements that have different polarization times, points on the magnetization $M_Z$ 10 curve may be derived, and thus, the T1 time for the particular formation may be determined. A receiver antenna (that may be formed from the same coil as the transmitter antenna) receives the train of spin echo signals 16 and stores digital signals that indicate the spin echo signals 16.

As an example, for the acquisition sequence, a typical logging tool may emit a pulse sequence based on the CPMG (Carr-Purcell-Meiboom-Gill) pulse sequence. The application of the CPMG pulse train includes first emitting an RF burst, called an RF pulse, that has the appropriate duration to rotate the magnetization, initially polarized along the $B_0$ field, by 90° into a plane perpendicular to the $B_0$ field. The RF pulse that rotates the magnetization by 90° is said to introduce a flip angle of 90°. Next, a train of equally spaced 180° RF pulses is transmitted. Each 180° RF pulse has the appropriate duration to rotate the magnet moment by 180° to refocus the spins to generate each spin echo signal 16. Each RF pulse that rotates the magnetization by 180° is said to introduce a flip angle of 180°. Individual hydrogen nuclei experience randomly time-varying magnetic environments during the pulse sequence, a condition that results in an irreversible loss of magnetization and a consequent decrease in successive echo amplitudes. The rate of loss of magnetization is characterized by a "transverse relaxation time" (called T2) and is depicted by the decaying envelope 12 of FIG. 1.

In general, the above NMR measurement of the T1 time may be referred to as a saturation recovery, or T1-based, measurement due to the fact that the nuclear spins are saturated (i.e., the magnetization is decreased to approximately zero) at the beginning of the wait time. Thus, from the NMR measurement, a value of the magnetization $M_Z$ 10 curve may be determined from the initial signal amplitude. In general, an NMR measurement of the signal decay may be labeled a T2-based measurement. It is noted that every T2 measurement is T1 weighted due to the fact that prepolarization occurs during the wait time before the acquisition sequence.

The initial amplitude of the envelope 12 is proportional to the product of the porosity and the hydrogen index of the formation fluids. The rate at which the envelope 12 decays is governed by the chemical nature of the fluids, the fluid viscosity, and the pore structure of the formation, which may be related to permeability. Standard data analysis involves fitting the echo amplitudes to a multi-exponential function. The coefficients which result from the fitting process constitute a relaxation time distribution, usually referred to as a T2 distribution. Small T2 values, deriving from fast relaxing components in the echo train, are generally associated with bound fluid, whereas large T2 values reflect free fluid. Total porosity is proportional to the area under the T2 distribution, which is identical to the initial amplitude of the multi-exponential function. Bound water can be identified with the short T2 components in the distribution, while free fluid generally contributes to the long T2 components.

The precision with which porosity, bound fluid, and free fluid volumes can be derived is determined by the intrinsic noise level of the measurement. In practice, it is usual to average NMR echo data over several depth levels in order to improve the signal-to-noise ratio (SNR) prior to inversion. This procedure improves the accuracy of the computed quantities but degrades the vertical resolution. In thin laminated beds, resolution can be critical for correct petrophysical evaluation, and in these situations, vertical averaging of measurements may be detrimental.

A processing technique for enhancing the vertical resolution of logging data is discussed in U.S. Pat. No. 4,794,792 (the '792 patent). The '792 patent discloses using one sensor to obtain an accurate, but low resolution measurement of some property of interest and using another sensor to obtain a less accurate but higher resolution measurement of the property. The '792 patent also discusses a technique called alpha processing to combine these two measurements to produce an accurate and high-resolution estimate of the property. However, the '792 patent does not teach generating an accurate, high resolution estimate without the use of multiple sensors: one for the high resolution and low accuracy measurement and another one for the lower resolution and higher accuracy measurement.

NMR log data is customarily processed by applying inversion algorithms to measured echo amplitude decays to yield distributions of transverse relaxation times. The inversion is generally a non-linear operation due to the positivity constraints, which are imposed on the individual populations of the relaxation time distribution. Consequently, both statistical and systematic errors in porosity estimates increase in a non-linear fashion with increasing noise levels. Therefore, to improve the signal-to-noise ratio (SNR) and thus, the accuracy of the data, the echo trains that are collected from different depths may be averaged together. However, this averaging effectively degrades the resolution provided by these echo trains.

A technique for more efficiently inverting NMR echo data using window-sums is disclosed in U.S. Pat. No. 5,291,137. This algorithm is described for non-linear inversion of data acquired at a single depth or for depth-averaged data.

Thus, there is a continuing need for a technique that addresses one or more of the problems that are stated above.

SUMMARY OF THE INVENTION

In an embodiment of the invention, a method that is usable with an NMR measurement apparatus includes averaging first spin echo trains acquired from different regions of a sample to form a second spin echo train. The first spin echo trains are used to produce a first estimate of a property of the sample, and this first estimate has a first resolution and a first accuracy. The second spin echo train is used to produce a second estimate of the property, and this second estimate has a second resolution that is lower than the first resolution and a second accuracy that is higher than the first accuracy. The first and second estimates are combined to produce a third estimate of the property. The third estimate has a third resolution near the first resolution of the first estimate and a third accuracy near the second accuracy of the second estimateAdvantages and other features of the invention will become apparent from the following description, drawing and claims.

BRIEF DESCRIPTION OF THE DRAWINGS

FIG. 5 is a full T2 distribution obtained by the inversion of depth averaged spin echo trains according to an embodiment of the invention.

FIG. 6 is a reduced T2 distribution derived from the full T2 distribution of FIG. 5 according to an embodiment of the invention.

FIG. 7 is an illustration of the use of window sums according to an embodiment of the invention.

FIG. 8 is a full T2 distribution according to an embodiment of the invention.

FIG. 9 depicts reduced T2 distributions according to an embodiment of the invention.

DETAILED DESCRIPTION

Figure 1:
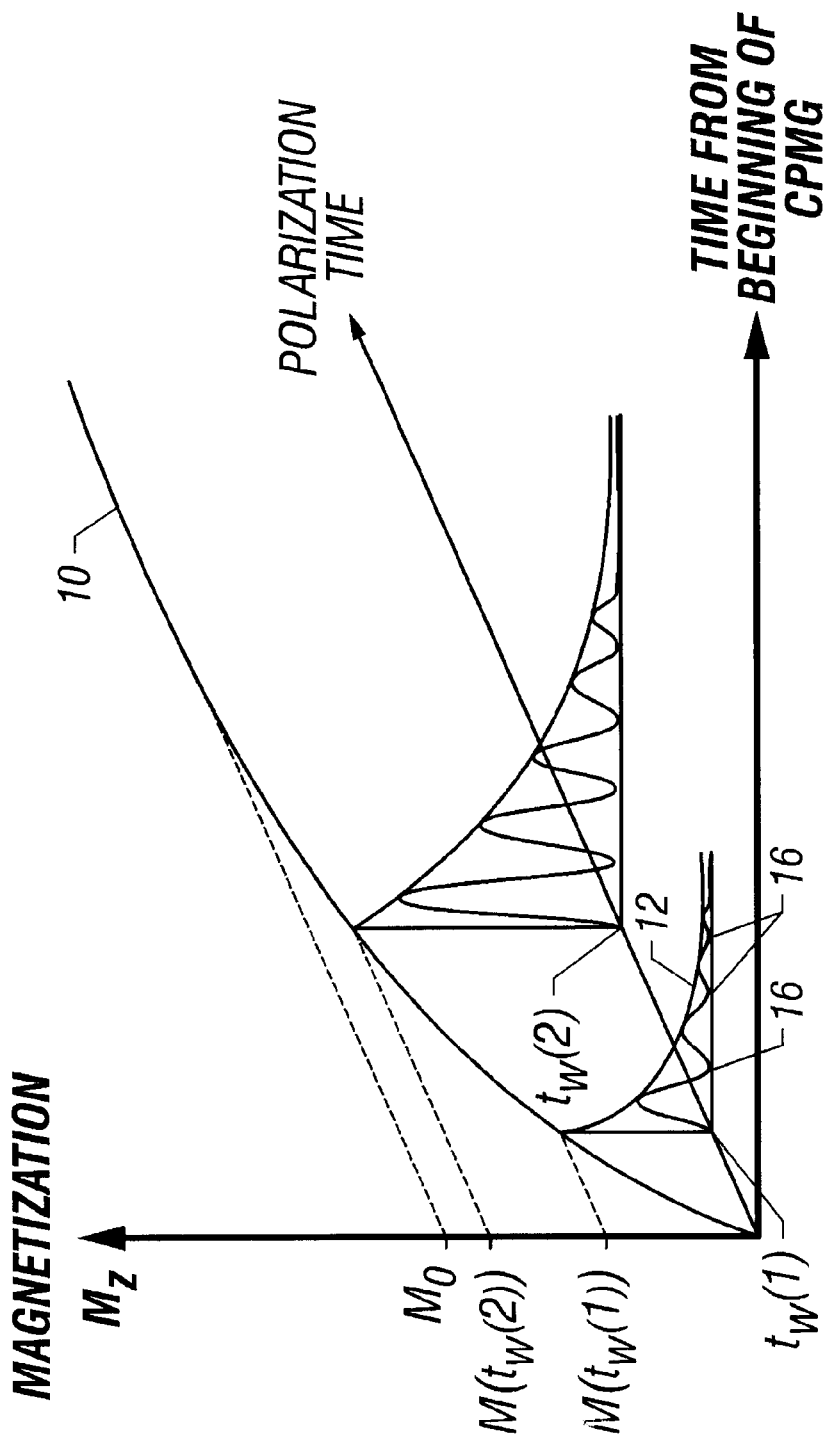
FIG. 1 is a graph of longitudinal magnetization illustrating T1 and T2 measurements of the prior art.
Figure 2:
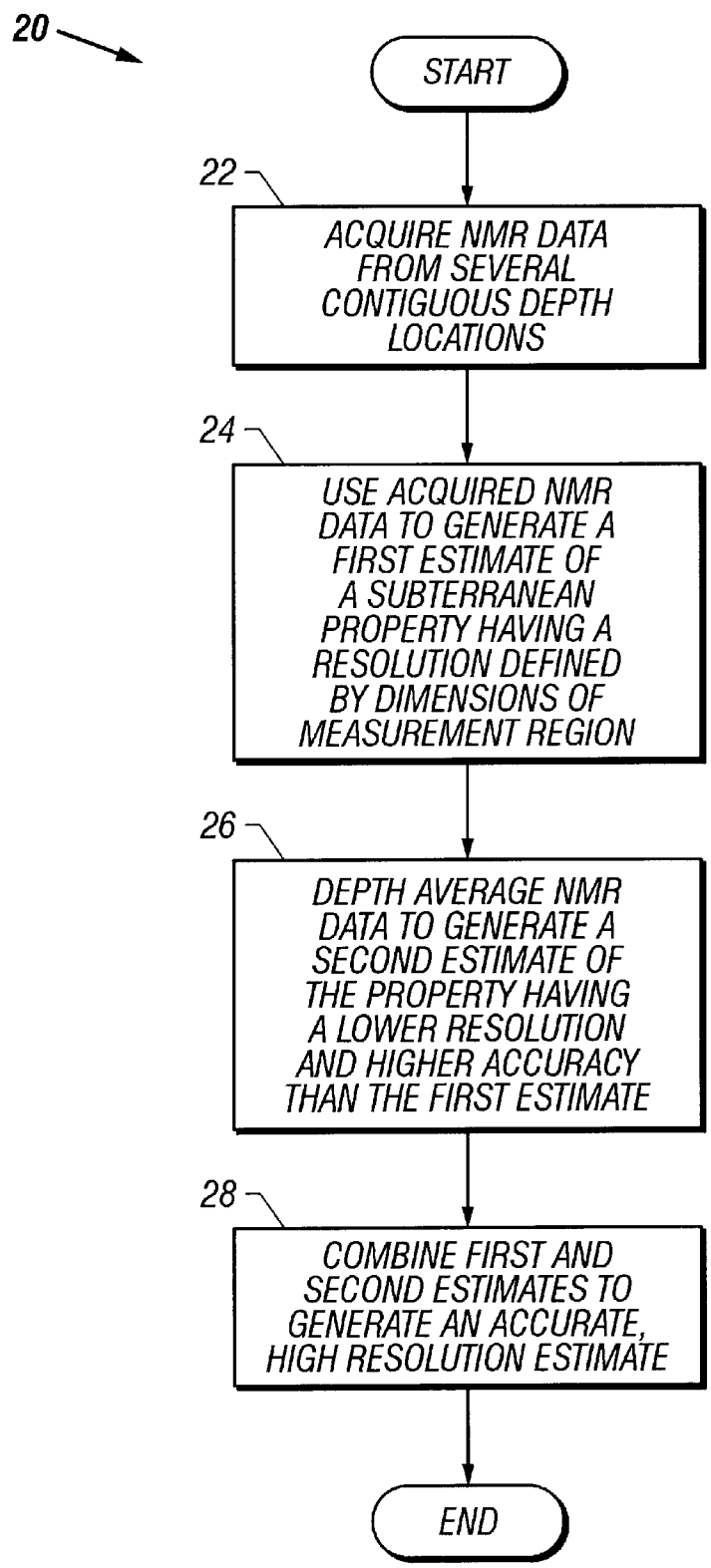
FIG. 2 is a flow diagram illustrating a technique to obtain estimates according to an embodiment of the invention.

Referring to FIG. 2, an embodiment 20 of a nuclear magnetic resonance (NMR) processing technique in accordance with the invention produces accurate and high resolution estimates of petrophyscial properties even though the NMR data that is used to produce the estimate may be acquired via a single antenna or sensor. An alpha processing technique (described herein) is used to produce these estimates, such as estimates for porosity, a bound fluid volume, a free fluid volume and a permeability.

More specifically, in some embodiments of the invention, the technique 20 includes acquiring (block 22) NMR data from several contiguous depth locations of a subterranean well. As example, the acquisition may include acquiring several NMR spin echo trains, each of which may be produced by a CPMG (Carr-Purcell-Meiboom-Gill) pulse sequence (for example) and is associated with a different one of the depth locations. Next, the technique includes using (block 24) the acquired NMR data to generate a first estimate of some subterranean property. This estimate has a resolution that is defined by the dimensions of the measurement region.

The acquired NMR data is also stacked, or depth averaged (block 26), to generate a second estimate of the property. This second estimate has a lower resolution than the first estimate due to the depth averaging. However, the depth averaging also improves the signal-to-noise ratio (SNR) of the estimate, and thus, the second estimate permits a higher accuracy than the first estimate. To generate an estimate that has an accuracy near the second estimate and a resolution near the first estimate, the technique 20 includes combining (block 28) the first and second estimates. This combination includes alpha processing, in some embodiments of the invention, as described below.

Figure 3:
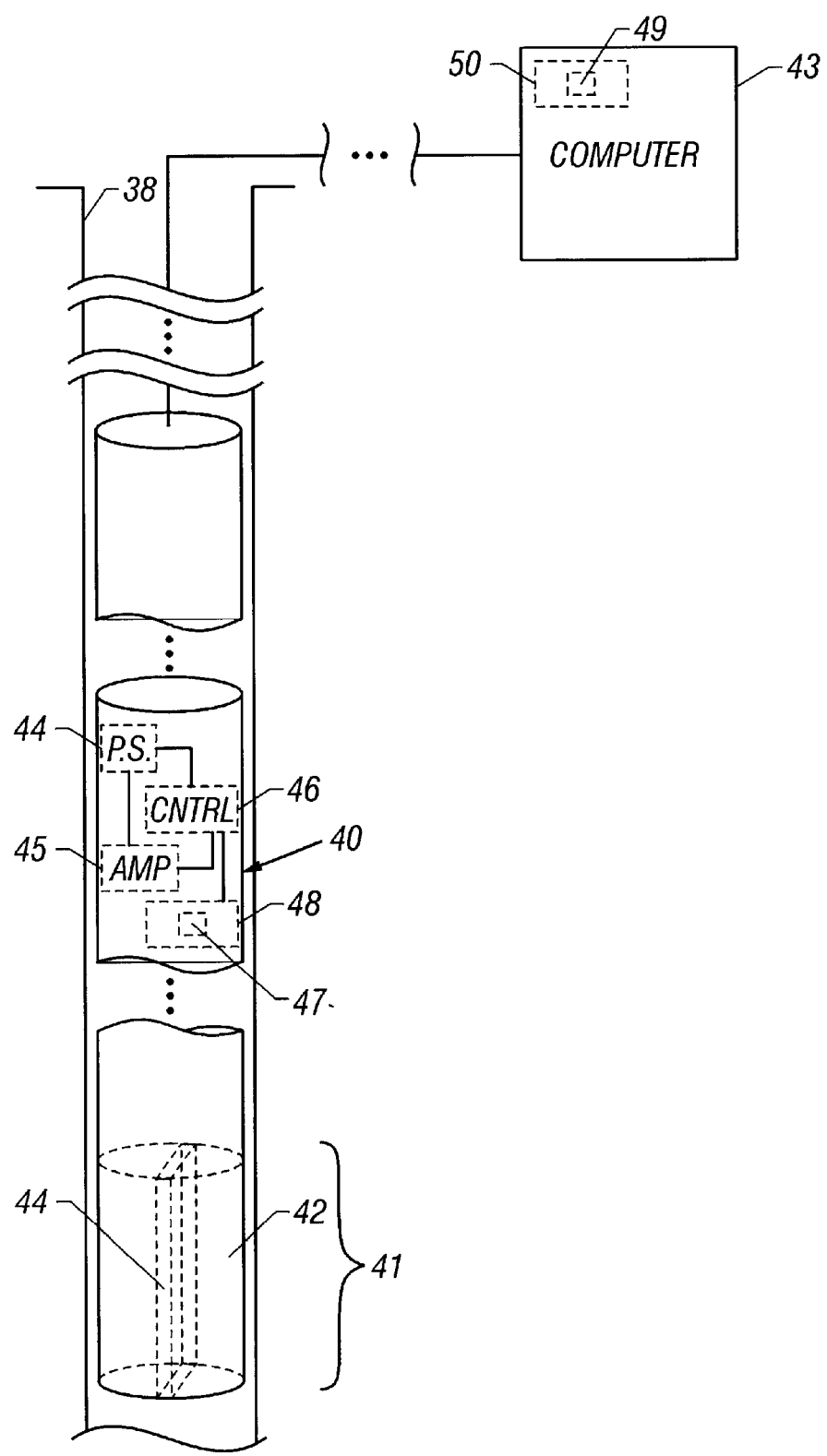
FIG. 3 is a schematic diagram of a well that contains an NMR measurement tool according to an embodiment of the invention.

FIG. 3 depicts a well 38 that may be logged by an NMR tool 40. In some embodiments of the invention, the NMR tool 40 may include a single NMR sensor 41 and a single receiving antenna 44 (of the NMR sensor 41) to receive indications of spin echo trains from the surrounding formation. The sensor 41 also includes a permanent magnet 42 for purposes of establishing a static magnetic field for NMR measurements. The tool 40 may include such circuitry as a control unit, or controller 46, that uses an amplifier 45 that is coupled to the controller 46 to generate radio frequency (RF) pulses that are transmitted via the antenna 44 (for example) into the surrounding formation to produce the received spin echo trains. The amplifier 45 and controller 46 may receive power from a power supply 44 of the circuitry.

In some embodiments of the invention, a computer 43 that is located at the surface of the well or located at another location receives data that is indicative of the spin echo trains. The computer 43 may include a control unit (a microprocessor, for example) that executes instructions 49 that are stored in a memory 50 of the computer 43 to process this data to perform one or more of the alpha processing techniques that are described herein. In other embodiments of the invention, the controller 46 may execute instructions 47 that are stored in a memory 48 of the tool 40 to perform one or more of the alpha processing techniques that are described herein; or the controller 46 and computer 43 may interact with each other to jointly perform these techniques, as just a few examples. As examples, the NMR tool 40 may be a wireline tool or a logging while drilling (LWD) tool.

Figure 4:
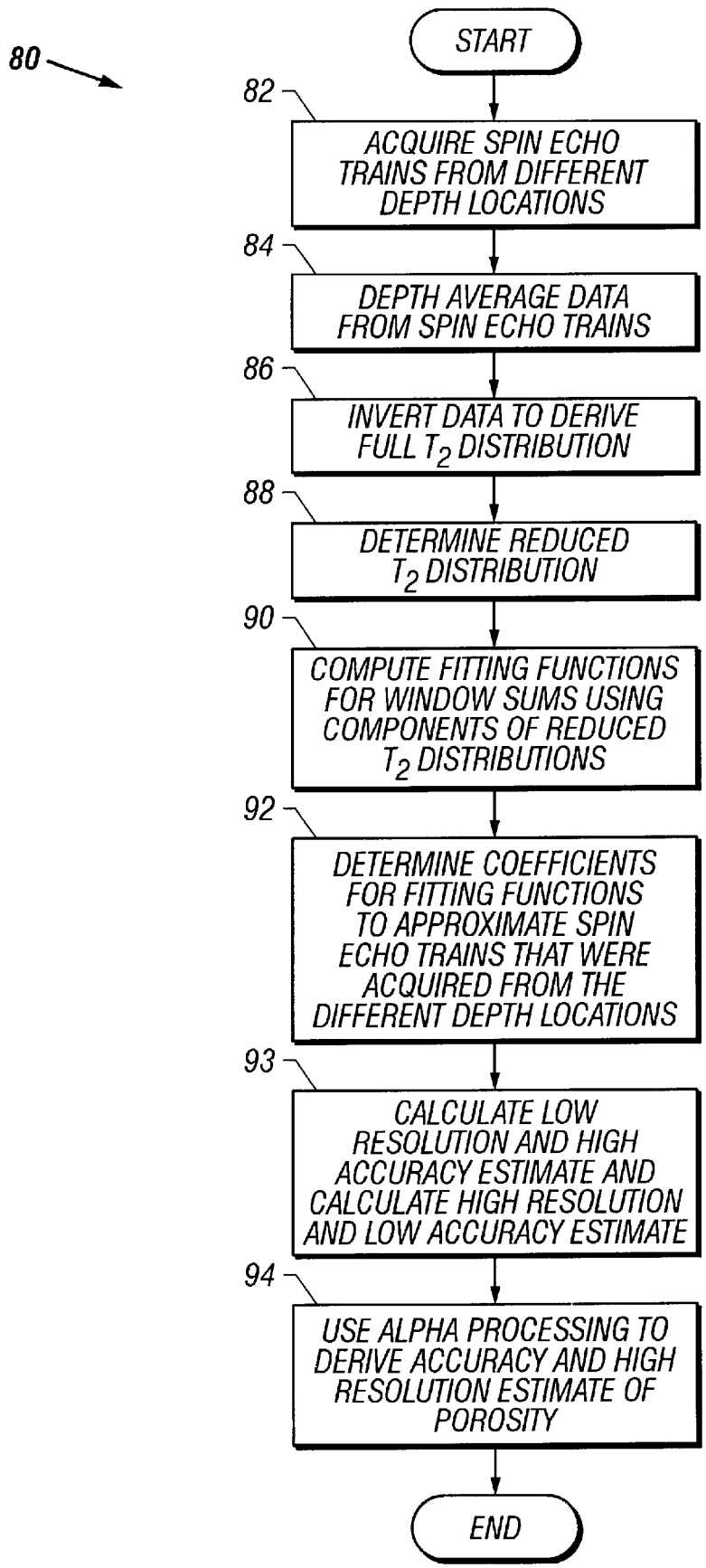
FIG. 4 is a flow diagram depicting a technique to determine a high resolution and accurate porosity estimate according to an embodiment of the invention.

FIG. 4 depicts a technique 80 to derive a high resolution and accurate estimation of a porosity according to embodiment of the invention. The technique 80 includes receiving, or acquiring (block 82), spin echo trains from different depths along the well bore. For example, the NMR tool 40 (see FIG. 3) may transmit the appropriate the appropriate tipping and refocusing NMR pulses (via the antenna 44) to establish successive CPMG sequences for purposes of acquiring multiple spin echo trains, each of which is associated with a different depth location due to the movement of the NMR tool 40. Echo decays from N adjacent depth measurements are subsequently depth averaged (block 84) to produce one depth-averaged echo decay, and this depth-averaged echo decay is inverted (block 86) to yield a T2 distribution (hereinafter referred to as "a full T2 distribution") for the depth interval that corresponds to N measurements. FIG. 5 depicts an exemplary full T2 distribution 110.

The technique 80 subsequently includes determining (block 88) a reduced T2 distribution, such as a reduced T2 distribution 130 (see FIG. 6) that is derived from the full T2 distribution 110. It is noted that the full T2 distribution 110 may have many more components 120 (30, for example) than the components 132 (four, for example) of the reduced T2 distribution 130. In some embodiments of the invention, the components 132 of the reduced T2 distribution 130 are selected to satisfy the following conditions: i) the T2 values for adjacent components differ by at least a predetermined difference, such as a factor between generally 2 to 3 (as an example); ii) each component 132 constitutes a predefined minimum of the total porosity; iii) the sum of amplitudes of the components 132 in the reduced T2 distribution equals the total porosity; and iv) the logarithmic mean for the reduced T2 distribution equals the logarithmic mean for the original T2 distribution.

As depicted in FIG. 6, the components 132 of the reduced T2 distribution 130 have approximately the same amplitude. Furthermore, the components 132 are generally unequally spaced apart. It is to be noted that the reduced T2 distribution 130 is a coarse-grained replica of the cumulative full T2 distribution 110. If the full T2 distribution contains just a single peak (a short T2 peak as observed in shale formations, for example), the reduced T2 distribution may contain just one or two components, as a result of conditions i) and ii) above.

Still referring to FIG. 4, the next part of the technique 80 includes recreating the echo trains for the N adjacent depths using the components of the reduced T2 distribution. To aid in these computation, fitting functions for window sums are then computed, as depicted in block 90. Referring also to FIG. 7, in this manner, in order to enhance computation efficiency, the data for each spin echo train is compressed by grouping the echoes of a particular spin echo train into windows 150 and adding the spin echoes of each window 150 together. The number of echoes in each window 150 is not critical and may be defined by the user. In some embodiments of the invention, the windows 150 increase in size approximately exponentially, beginning with the first echoes, as illustrated in FIG. 7. It is noted that the windowsums procedure that is described herein may be used for purposes of efficiency. However, the use of window sums is not necessary, as the general method could equally be applied using individual echo amplitudes as data points. Other data compression methods, such as SVD, may also be used.

For each of the T2 values that are defined in the reduced T2 distribution, the fitting functions are computed. In general, in some embodiments of the invention, the fitting functions are of the following form:

$$F_1(k, j) = (1 - e^{-WT(j)\chi_Z T_{2,i}}) \sum_{n=n1(k)}^{n2(k)} e^{-nTE/T_{2,i}}$$

where "n1(k)" and "n2(k)" are the first and last echoes of the kth window-sum, "WT(j)" is the jth wait time, "$\chi$" is the T1/T2 ratio (assumed to be single-valued), "TE" is the echo spacing and the subindex "i" refers to a specific component in the reduced distribution whose relaxation time is "$T_{2,i}$". Note that the fitting functions are the same for all of the depths that are included in the vertical averaging. If only one wait-time is used and this provides full polarization, then the term in parentheses on the right hand side of Equation 2 can be omitted, and the index j may be dropped. If echo data for a particular wait time is acquired several times, the averaged echo amplitudes from all the repeat acquisitions should be used. For dual or multi-wait-time acquisition, a value for $\chi$ may be available from inversion of the stacked data. In the case of single-wait-time data, $\chi$ may be estimated based on the downhole temperature and prior knowledge of the expected formation and drilling fluids. Alternatively, the term in parentheses on the right of Equation 2 may be omitted during fitting of the echo decays and a polarization correction, based on an assumed $\chi$ value, can be applied to the final porosity values. If this approach is taken, the depth-averaged full T2 distribution should not include any polarization correction. This method is preferred for single wait-time data, since the effective T1/T2 ratios for reduced and full T2 distributions may not be identical.

After the fitting functions for the window sums are computed, the technique 80 next includes determining coefficients for the fitting functions to approximate the spin echo trains that were acquired from the different depth locations, as depicted in block 92 of FIG. 4. It is assumed that the echo train at each individual depth may be well-represented by a linear combination of the fitting functions, $F_i$ (k,j). If $\chi$ (m,j,k) is the value of the kth window-sum for the jth wait time at depth m, then the following relationship exists:

$$X(m, k, j) = \sum_i c_i(m) F_i(k, j)$$

where "$c_i$ (m)" is the amplitude of the ith T2 component at depth m. At a single depth, the most likely combination of $c_i$ (m) can be determined by minimizing an error function that is described below:

$$\varepsilon^2 = \sum_{k,j} \left[ \frac{X(m, k, j) - \sum_i c_i(m) F_i(k, j)}{\sqrt{(1 + n2(k) - n1(k))/N_j}} \right]^2$$

where "$N_j$" is the number of repeat acquisitions made for the jth wait-time. The denominator on the right hand side of Equation 4 ensures that each window-sum is correctly weighted according to its statistical error. The coefficients, $c_i$ (m), at depth m, can be obtained by solving a set of linear equations, as described below:

$$Sc(m) = u(m)$$

where "c(m)" is a vector with elements, $c_i$ (m) and "S" is a matrix whose elements are computed from the fitting functions described below:

$$S(i1, i2) = \sum_{k,j} F_{i1}(k, j) F_{i2}(k, j) + \lambda \delta_{i1,i2}$$

in which
$\lambda$
is a regularization parameter and $\delta_{i1,i2} = 1$ if i1=i2 but is zero otherwise. The elements of vector, u(m), are computed from the measured data $$u(m, i) = \sum_{k,j} X(m, k, j) F_i(k, j)$$

For each depth, m, included in an averaging interval, a set of equations of the form that is described by Equation 5 are set up. In addition, a set of coupling equations may be formulated, which constrain the sum of the coefficients, $c_i$ (m), over all depths, m, to equal the component, $C_i$, corresponding to the amplitude of the $T_{2i}$ component in the stacked reduced distribution, as described below:

$$\sum_m c_i(m) = C_i$$

The constraint that is established by Equation 8 corresponds to the alpha-processing aspect of the technique. In this manner, if vertical averaging is performed over $N_D$ depths and there are $N_C$ components in the reduced T2 distribution, there are a total of $(N_D+1)*N_C$ equations with just $N_D*N_C$ unknowns, namely the individual components, $c_i$ (m). Solutions to this set of equations can be obtained using standard methods.

Referring to FIGS. 8 and 9, thus, to summarize, at this point, a spin echo train 170 at each depth has been fitted using only components of a reduced T2 distribution 168 that is derived from a full T2 distribution 167 that, in turn, was produced by inverting the spin echo train that was generated by depth-averaging the spin echo trains 170. Therefore, the inversion of each curve that approximates a spin echo signal 170 produces a T2 distribution 180 that has coefficients for the same T2 values as the reduced T2 distribution 168. As described below, the sum of the coefficients for the same T2 time for all of the T2 distributions 180 equals the corresponding coefficient of the reduced T2 distribution 168.

The technique 80 next includes calculating a low resolution and high accuracy estimate for the porosity and calculating a high resolution and lower accuracy estimate for the porosity, as depicted in block 93 of FIG. 4. In this manner, once the individual components $c_i$ (m) of the T2 distribution for the spin echo signal at each depth are calculated, the high resolution and low accuracy estimate may be calculated by adding the $c_i$ (m) coefficients at each depth, as described below:

$$\Phi(m) = \sum_i c_i(m)$$

Thus, the porosity calculated at each depth has a high resolution but a reduced accuracy. The low resolution but high accuracy estimate of the porosity is obtained by summing the components of the reduced T2 distribution. Alpha processing is used (block 94 of FIG. 4) with these estimates to derive an accurate and high resolution indication of the porosity of along the wellbore. The alpha processing is performed concurrently with the formation of the estimates, in some embodiments of the invention.

Figure 11:
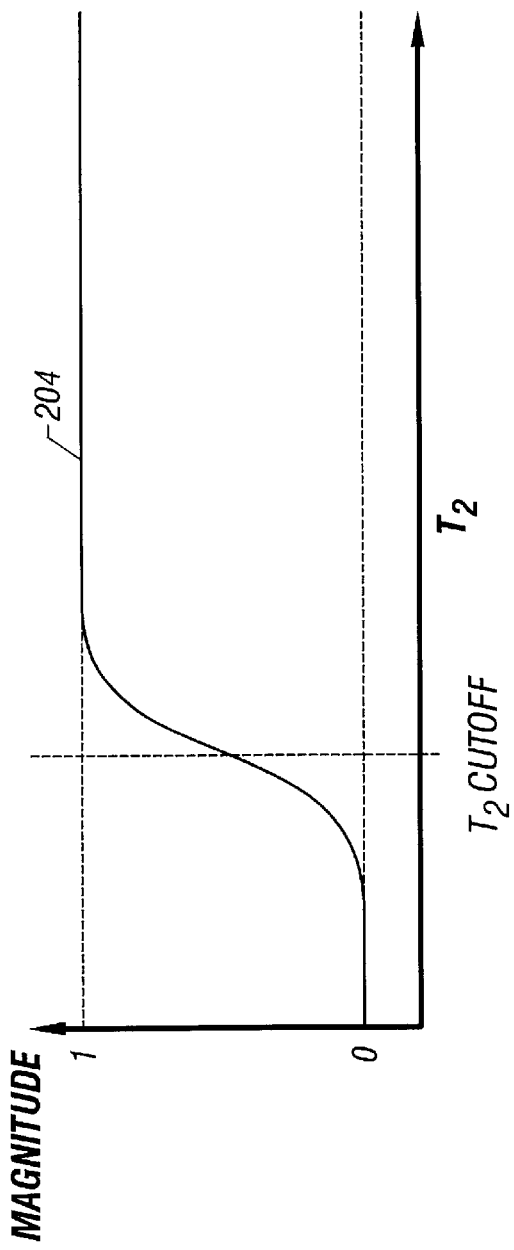
FIG. 11 is a plot of a linear free-fluid estimator versus echo number and a plot of echo amplitudes versus echo number according to an embodiment of the invention.
Figure 12:
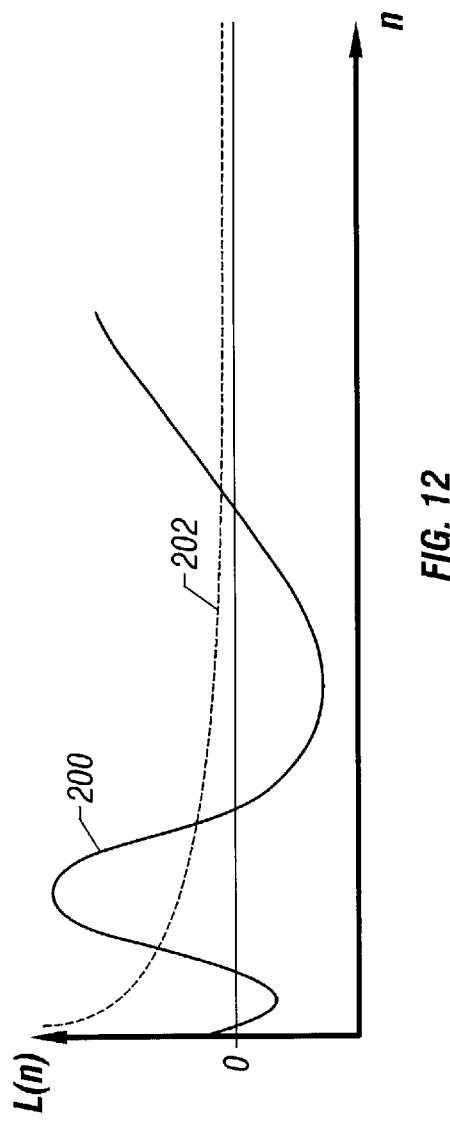
FIG. 12 is a plot of a free-fluid cutoff function versus T2 according to an embodiment of the invention.

If polarization correction was included in the fitting functions (Equation 2), then the porosity value in Equation 9 represents the full high-resolution porosity estimate. Otherwise, a polarization correction may be necessary. This correction is applied to the free fluid component and is described below. Division of porosity into bound fluid and free fluid components is performed by obtaining a high-resolution estimate for the free fluid volume. This quantity can generally be determined with good precision since the free fluid contributes signal to many echoes (it has long T2 values) and therefore, has high effective signal-to-noise ratio. In principle, any robust inversion algorithm should provide a reliable estimate of the free fluid volume. For example, one efficient and high-precision method involves the use of linear estimators, which take linear combinations of echo amplitudes. If the nth echo amplitude at depth m is A(m,n), the corresponding free fluid volume estimate, without polarization correction, is $$FFV_0^*(m) = \sum_n L(n)A(m,n)$$

where "L(n)" is a linear free fluid estimator function. Referring to FIG. 11, in some embodiments of the invention, the inverted linear estimator function, in the T2 domain, may have coefficients that are approximately zero below the T2 free-fluid/bound-fluid cutoff, and the coefficients transition near the T2 cutoff to assume a value of approximately one for T2 times above the T2 cutoff. As examples, the linear estimator function may the waveform 200 that is depicted in FIG. 12 and may be used to filter low T2 values from a spin echo train 202.

Alpha processing may be applied to correct for possible discrepancies between the high-resolution linear estimates and any non-linear estimates (called $FFV_0$ (NL) and FFV (NL) below) computed for depth-averaged data with standard processing, as described below:

$$FFV_0(m) = \left(\frac{N_0 FFV_0^*(m)}{\sum_m FFV_0^*(m)}\right) \times FFV_0(NL)$$

$$FFV(m) = \left(\frac{N_0 FFV_0^*(m)}{\sum_m FFV_0^*(m)}\right) \times FFV(NL)$$

The subindex "0" in Equations 11 and 12 indicates that these quantities do not include any polarization correction. Quantities with no subindex imply that polarization correction has been applied, so that Equation 12 provides a fully-corrected high-resolution free-fluid volume estimate. Note that any robust high-resolution estimates may be used for $FFV_0^*(m)$ in equation 11. The use of linear estimators is suggested here simply because of their good precision, efficiency and ease of implementation.

Computation of high resolution bound-fluid volumes is now straightforward. If total porosity estimates, $\Phi(m)$, have been computed with polarization correction included, the bound fluid volume is described by the following equation:

$$BFV(m) = \Phi(m) - FFV(m)$$

If the total porosity estimates do not include polarization correction, then $$BFV(m) = \Phi(m) - FFV_D(m)$$

Although emphasis has been placed on the determination of bound-fluid and free-fluid volumes, other high-resolution quantities may also be derived using the strategy outlined here. In particular, high-resolution estimates for the logarithmic mean $T_2$, SDR permeability and Timur-Coates permeability can also be derived:

$$\ln[T_{2\,SDR}(m)] = \frac{\sum_i c_i(m) \ln[T_u]}{\sum_i c_i(m)}$$

$$K_{SDR} = a[\Phi(m)]^b [T_{2\,101}(m)]^c$$

$$K_{TC} = a'[\Phi(m)]^{b'} \left[\frac{FFV(m)}{BFV(m)}\right]^{c'}$$

In these expressions, the parameters "a," "b," "c," "a'", "b'" and "c'" are adjustable parameters. Ideally, these should be calibrated for each well or region from which NMR data is acquired. Typical values are a=10$^4$ mD, a''=4 mD/ms$^2$, b=b''=4 and c=c''=2.

Figure 10:
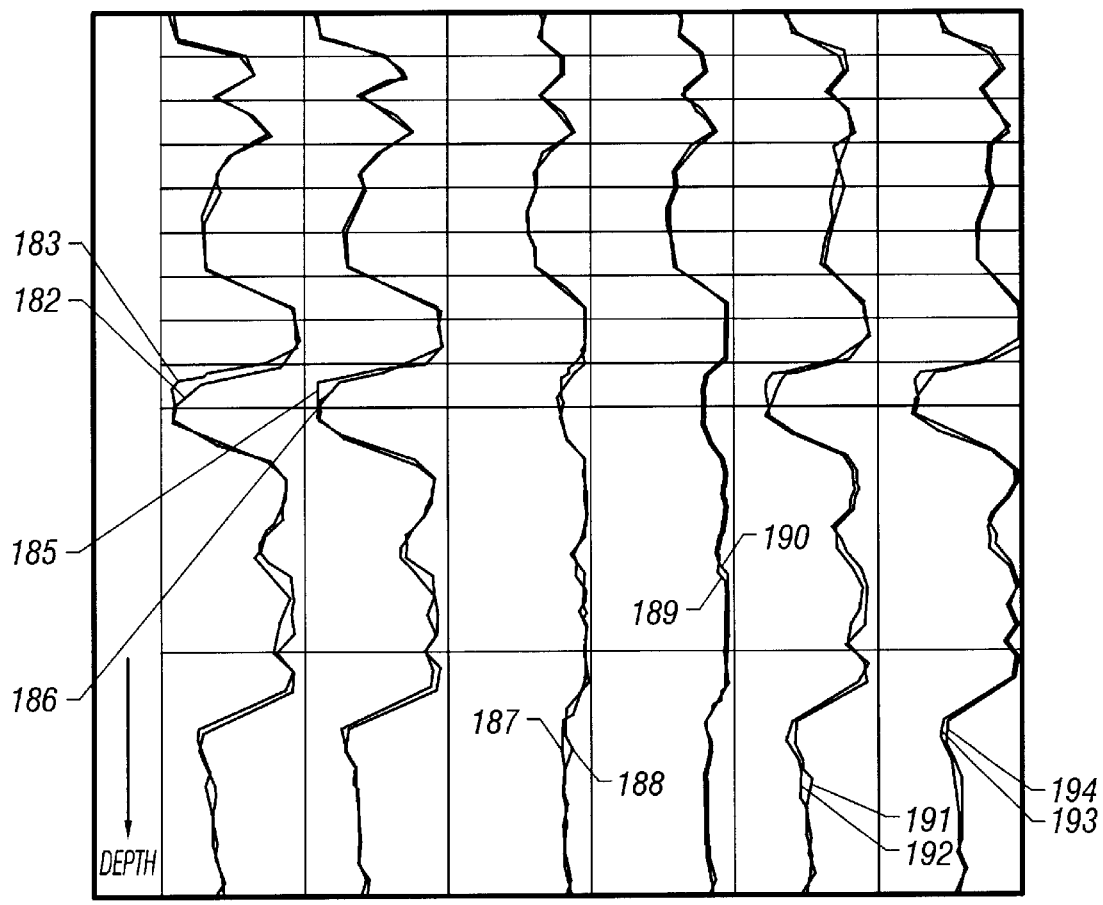
FIG. 10 is a well log depicting use of the technique of FIG. 2 and comparison of the use to the use of conventional techniques.

FIG. 10 is a well log depicting use of the techniques that are described herein and a comparison of the use to the use of conventional techniques. The echo sequence used to produce this log includes one long wait time acquisition with 1800 echoes, followed by 10 repeat acquisitions with a 20 ms wait-time and 30 echoes. This sequence is designed to improve accuracy and precision on short T2 components. Shown in the log are two curves 185 and 186 (obtained using two passes) for the total porosity (TCMR) using a technique that is described herein; two curves 182 and 183 (obtained using two passes) for TCMR using a conventional technique; two curves 189 and 190 (obtained using two passes) for the free fluid volume (CMFF) using a technique that is described herein; two curves 187 and 188 (obtained using two passes) for the CMFF using a conventional technique; two curves 193 and 194 (obtained using two passes) for the bound fluid volume (BFV) using a technique that is described herein; and two curves 191 and 192 (obtained using two passes) for the BFV using a conventional technique; Vertical averaging over 5 levels was employed for the standard processing of averaged data.

While the invention has been disclosed with respect to a limited number of embodiments, those skilled in the art, having the benefit of this disclosure, will appreciate numerous modifications and variations therefrom. It is intended that the appended claims cover all such modifications and variations as fall within the true spirit and scope of the invention.

What is claimed is:

1. A method for determining nuclear magnetic resonance properties of a sample of an earth formation with an NMR logging tool for receiving spin echo signals in response to generated NMR signals, comprising:
   averaging first spin echo trains acquired from different vertical regions of the sample to form a second spin echo train;
   calculating a first relaxation time distribution of a property of the sample from the first spin echo trains, the first relaxation time distribution having a first vertical resolution and a first accuracy;
   calculating a second relaxation time distribution from the second spin echo train, the second relaxation time distribution having a second vertical resolution lower than the first vertical resolution and a second accuracy higher than the first accuracy; and
   combining the first and second relaxation time distributions to produce a third relaxation time distribution, the third relaxation time distribution having a third vertical resolution near the first vertical resolution of the first relaxation time distribution and a third accuracy near the second accuracy of the second relaxation time distribution.

2. The method of claim 1, wherein the sample comprises at least one subterranean formation and the property comprises a petrophysical property.

3. The method of claim 1, wherein the property comprises a porosity.

4. The method of claim 1, wherein the property comprises a free-fluid volume.

5. The method of claim 1, wherein the property comprises a bound-fluid volume.

6. The method of claim 1, wherein the combining comprises:
using alpha processing to combine the first and second relaxation time distributions to produce the third relaxation time distribution.

7. The method of claim 1, wherein the acquiring comprises:
using an antenna to receive echo signals indicative of the first echo trains.

8. The method of claim 1, wherein the act of calculating the first relaxation time distribution comprises:
inverting the second echo train to generate a first T2 distribution having a first number of components;
generating a second T2 distribution from the first T2 distribution having a second number of components less than the first number of components of the first T2 distribution;
for each first echo train, using the components of the second T2 distribution to derive an associated T2 distribution that produces an associated curve that approximates the first echo train; and
summing components of each associated T2 distribution to produce the first relaxation time distribution.

9. The method of claim 8, wherein the first relaxation time distribution is used to calculate a porosity.

10. The method of claim 1, wherein the act of calculating the second relaxation time distribution comprises:
summing components of the second T2 distribution together.

11. The method of claim 1, wherein the act of using the first echo trains to produce the first relaxation time distribution comprises:
for each first echo train, summing combinations of amplitudes of the first echo train to produce the first relaxation time distribution; and
summing combinations of amplitudes of the second echo train to produce the second relaxation time distribution.

12. The method of claim 11, wherein the act of summing the amplitudes for each first echo train comprises:
applying a linear estimator function to filter T2 components below a predetermined T2 cutoff time.

13. The method of claim 1, wherein the property comprises a porosity.

14. The method of claim 1, wherein the property comprises a bound fluid volume.

15. The method of claim 1, wherein the property comprises a free fluid volume.

16. The method of claim 1, wherein the property comprises a logarithmic mean T2.

17. An NMR measurement apparatus for determining nuclear magnetic resonance properties of a sample of an earth formation with an NMR logging tool for receiving spin echo signals in response to generated NMR signals, comprising:
an antenna;
a controller coupled to the antenna and adapted to:
acquire a first set of spin echo trains from different adjacent vertical regions of the sample;
average the first set of spin echo trains to form a second spin echo train;
calculate a first relaxation time distribution of a property of the sample from the first set of spin echo trains, the first relaxation time distribution having a first vertical resolution and a first accuracy;
calculate a second relaxation time distribution from the second spin echo train, the second relaxation time distribution having a second vertical resolution lower than the first resolution and a second accuracy higher than the first accuracy; and
combine the first and second relaxation time distributions to produce a third relaxation time distribution, the third relaxation time distribution having a third vertical resolution near the first vertical resolution of the first relaxation time distribution and a third accuracy near the second accuracy of the second relaxation time distribution.

18. The NMR measurement apparatus of claim 17, wherein the sample comprises at least one subterranean formation and the property comprises a petrophysical property.

19. The NMR measurement apparatus of claim 17, wherein the property comprises a porosity.

20. The NMR measurement apparatus of claim 17, wherein the property comprises a free-fluid volume.

21. The NMR measurement apparatus of claim 17, wherein the property comprises a bound-fluid volume.

22. The NMR measurement apparatus of claim 17, wherein the controller uses alpha processing to combine the first and second relaxation time distribution to produce the third relaxation time distribution.

23. The NMR measurement apparatus of claim 17, wherein the apparatus comprises a wireline downhole tool.

24. The NMR measurement apparatus of claim 17, wherein the apparatus comprises a logging while drilling tool.

25. The NMR measurement apparatus of claim 17, wherein the controller uses the first echo trains to produce a first relaxation time distribution by inverting the second echo train to generate a first T2 distribution having a first number of components; generating second T2 distribution from the first T2 distribution having a second number of components less than the first number of components of the first T2 distribution; for each first echo train, using the components of the second T2 distribution to derive an associated T2 distribution that produces an associated curve that approximates the first echo train; and summing components of each associated T2 distribution to produce the first relaxation time distribution.

26. The NMR measurement apparatus of claim 25, wherein the first relaxation time distribution is used to calculate a porosity.

27. The NMR measurement apparatus of claim 25, wherein the controller uses the second echo train to produce the second relaxation time distribution by summing components of the second T2 distribution together.

28. The NMR measurement apparatus of claim 17, wherein the controller uses the first echo trains to produce the first relaxation time distribution by for each first echo train, summing up combinations of amplitudes of the first echo train to produce the first relaxation time distribution; and summing up the combinations of amplitudes of the second echo train to produce the second relaxation time distribution.

29. The NMR measurement apparatus of claim 17, wherein the controller sums the amplitudes for each first echo train by applying a linear estimator function to filter T2 components below a predetermined T2 cutoff time.

30. The NMR measurement apparatus of claim 17, wherein the property comprises a logarithmic mean T2.

31. The NMR measurement apparatus of claim 17, wherein the property comprises a free fluid volume.

32. The NMR measurement apparatus of claim 17, wherein the property comprises a bound fluid volume.

33. The NMR measurement apparatus of claim 17, wherein the property comprises a porosity.

34. An article comprising a computer readable storage medium storing instructions to cause a control unit to:

average first spin echo trains acquired from different vertical regions of a sample to form a second spin echo train;

the first spin echo trains to produce a first estimate of a property of the sample, the first estimate having a first vertical resolution and a first accuracy;

use the second spin echo train to produce a second estimate of the property, the second estimate having a second vertical resolution lower than the first resolution and a second accuracy higher than the first accuracy; and combine the first and second estimates to produce a third estimate of the property, the third estimate having a third vertical resolution near the first resolution of the first estimate and a third accuracy near the second accuracy of the second estimate.

35. The article of claim 34, wherein the storage medium stores instructions to cause the control unit:

use alpha processing to combine the first and second estimates to produce the third estimate.

36. The article of claim 34, wherein the storage medium stores instructions to cause the control unit to:

invert the second echo train to generate a first T2 distribution having a first number of components;

generate second T2 distribution from the first T2 distribution having a second number of components less than the first number of components of the first T2 distribution;

for each first echo train, use the components of the second T2 distribution to derive an associated T2 distribution that produces an associated curve that approximates the first echo train; and sum components of each associated T2 distribution to produce the first estimate.

37. The article of claim 36, wherein the storage medium stores instructions to cause the control unit to sum components of the second T2 distribution together to produce the second estimate.

38. The article of claim 34, wherein the storage medium stores instructions to cause the control unit to:

for each first echo train, sum up amplitudes of the first echo train to produce the first estimate; and sum up the amplitudes of the second echo train to produce the second estimate.

39. A method for determining nuclear magnetic resonance properties of an earth formation from spin echo measurements made at a plurality of vertical positions within the earth formations, comprising:

stacking a first selected number of the spin echo measurements;

generating a first relaxation time distribution from the stacked measurements, the first distribution having a first selected number of relaxation time components;

generating a second relaxation time distribution from the first distribution, the second distribution having fewer relaxation time components than the first distribution;

calculating, from the components in the second distribution, a spin echo amplitude train corresponding to each of the selected spin echo measurements, the calculating comprising adjusting an amplitude of each of the components in the second distribution such that each calculated spin echo train substantially matches each corresponding spin echo measurement, wherein an average of corresponding adjusted component amplitudes substantially equals each corresponding component amplitude in the second distribution.

40. The method of claim 39 wherein the spin echo measurements each comprise a Carr-Purcell-Meiboom-Gill sequence.

41. The method of claim 39 further comprising estimating at least one petrophysical property from each calculated spin echo train.

42. The method of claim 41 wherein the at least one petrophysical property comprises at least one of porosity, permeability, free fluid volume and bound fluid volume.

43. The method of claim 39 wherein the first distribution and the second distribution have substantially equal logarithmic means and component amplitude sums.

44. The method of claim 39 further comprising estimating at least one petrophysical property from the stacked spin echo measurements.

45. The method of claim 44 wherein the at least one petrophysical property comprises at least one of porosity, permeability, free fluid volume and bound fluid volume.

46. The method of claim 39 further comprising selecting a second selected number of spin echo measurements and repeating the stacking, the generating the first and second distributions and the calculating the corresponding spin echo trains for each of the second selected number of spin echo measurements.

47. The method of claim 46, wherein the second selected number of measurements includes measurements corresponding to at least one position not present in the first selected number of measurements, and the first selected number of measurements includes measurements corresponding to at least one position not present in the second selected number of locations.

48. The method of claim 46 wherein the second selected number of spin echo measurements each comprises a Carr-Purcell-Meiboom-Gill sequence.

49. The method of claim 46 further comprising estimating at least one petrophysical property from each calculated spin echo train corresponding to the first and second selected number of measurements.

50. The method of claim 39 wherein the at least one petrophysical property comprises at least one of porosity, permeability, free fluid volume and bound fluid volume.

51. The method of claim 46 wherein the first distribution and the second distribution determined from the spin echo measurements from the first selected number of measurements have substantially equal logarithmic means and component amplitude sums and the first distribution and the second distribution determined from the spin echo measurements from the second selected number of measurements have substantially equal logarithmic means and component amplitude sums.

52. The method of claim 46 further comprising estimating at least one petrophysical property from the stacked spin echo measurements of the second selected number of measurements.

53. The method of claim 52 wherein the at least one petrophysical property comprises at least one of porosity, permeability, free fluid volume and bound fluid volume.

54. The method of claim 39 wherein the first and second relaxation time distributions comprise transverse relaxation time.

55. A computer program disposed on a computer-readable storage medium, the program comprising instructions to cause a computer to process data from nuclear magnetic resonance spin echo measurements made at a plurality of vertical positions within earth formations, the program comprising instructions to cause the computer to:
stack a first selected number of the spin echo measurements;
generate a first relaxation time distribution from the stacked measurements, the first distribution having a first selected number of relaxation time components;
generate a second relaxation time distribution from the first distribution, the second distribution having fewer relaxation time components than the first distribution;
calculate, from the components in the second distribution, a spin echo amplitude train corresponding to each of the selected spin echo measurements, the calculating comprising adjusting an amplitude of each of the components in the second distribution such that each calculated spin echo train substantially matches each corresponding spin echo measurement, wherein an average of corresponding adjusted component amplitudes substantially equals each corresponding component amplitude in the second distribution.

56. The computer program of claim 55 wherein the spin echo measurements each comprise a Carr-Purcell-Meiboom-Gill sequence.

57. The computer program of claim 55 further comprising instructions to cause the computer to estimate at least one petrophysical property from each calculated spin echo train.

58. The computer program of claim 57 wherein the at least one petrophysical property comprises at least one of porosity, permeability, free fluid volume and bound fluid volume.

59. The computer program of claim 55 wherein the first distribution and the second distribution have substantially equal logarithmic means and component amplitude sums.

60. The computer program of claim 55 further comprising instructions to cause the computer to estimate at least one petrophysical property from the stacked spin echo measurements.

61. The computer program of claim 60 wherein the at least one petrophysical property comprises at least one of porosity, permeability, free fluid volume and bound fluid volume.

62. The computer program of claim 55 further comprising instructions to cause the computer to select a second selected number of spin echo measurements and to repeat the stacking, the generating the first and second distributions and the calculating the corresponding spin echo trains for each of the second selected number of spin echo measurements.

63. The computer program of claim 62, wherein the second selected number of measurements includes measurements from at least one position not present in the first selected number of measurements, and the first selected number of measurements includes measurements from at least one position not present in the second selected number of locations.

64. The computer program of claim 62 wherein the spin echo measurements each comprise a Carr-Purcell-Meiboom-Gill sequence.

65. The computer program of claim 62 further comprising instructions to cause the computer to estimate at least one petrophysical property from each calculated spin echo train in the second selected number of measurements.

66. The computer program of claim 65 wherein the at least one petrophysical property comprises at least one of porosity, permeability, free fluid volume and bound fluid volume.

67. The computer of claim 62 wherein the first distribution and the second distribution determined from the spin echo measurements from the first selected number of measurements have substantially equal logarithmic means and component amplitude sums, and the first distribution and the second distribution determined from the spin echo measurements from the second selected number of measurements have substantially equal logarithmic means and component amplitude sums.

68. The computer program of claim 62 further comprising instructions to cause the computer to estimate at least one petrophysical property from the stacked spin echo measurements from the second selected number of measurements.

69. The computer program of claim 68 wherein the at least one petrophysical property comprises at least one of porosity, permeability, free fluid volume and bound fluid volume.

70. The computer program of claim 62 wherein the first and second relaxation time distributions comprise transverse relaxation time.

71. A method for nuclear magnetic resonance well logging, comprising:
moving a nuclear magnetic resonance well logging instrument along a wellbore and making spin echo measurements at a plurality of depth levels within the wellbore;
stacking a first sleeted number of the spin echo measurements;
generating a first relaxation time distribution from the stacked measurements, the first distribution having a first selected number of relaxation time components;
generating a second relaxation time distribution from the first distribution, the second distribution having fewer relaxation time components than the first distribution;
calculating, from the components in the second distribution, a spin echo amplitude train corresponding to each of the selected spin echo measurements, the calculating comprising adjusting an amplitude of each of the components in the second distribution such that each calculated spin echo train substantially matches each corresponding spin echo measurement, wherein an average of corresponding adjusted component amplitudes substantially equals each corresponding component amplitude in the second distribution.

72. The method of claim 71 wherein the spin echo measurements each comprise a Carr-Purcell-Meiboom-Gill sequence.

73. The method of claim 71 further comprising estimating at least one petrophysical property from each calculated spin echo train.

74. The method of claim 73 wherein the at least one petrophysical property comprises at least one of porosity, permeability, free fluid volume and bound fluid volume.

75. The method of claim 71 wherein the first distribution and the second distribution have substantially equal logarithmic means and component amplitude sums.

76. The method of claim 71 further comprising estimating at least one petrophysical property from the stacked spin echo measurements.

77. The method of claim 76 wherein the at least one petrophysical property comprises at least one of porosity, permeability, free fluid volume and bound fluid volume.

78. The method of claim 71 further comprising moving the instrument along the wellbore, selecting a second selected number of spin echo measurements and repeating the stacking, the generating the first and second distributions and the calculating the corresponding spin echo trains for each of the second selected, number of spin echo measurements.

79. The method of claim 78, wherein the second selected number of spin echo measurements includes measurements from at least one depth level not present in the first selected number of measurements, and the first selected number of measurement includes measurements from at least one depth level not present in the second selected number of measurements.

80. The method of claim 79 wherein the spin echo measurements of the second selected number of measurements each comprise a Carr-Purcell-Meiboom-Gill sequence.

81. The method of claim 79 further comprising estimating at least one petrophysical property from each calculated spin echo train.

82. The method of claim 81 wherein the at least one petrophysical property comprises at least one of porosity, free fluid volume and bound fluid volume.

83. The method of claim 81 wherein the first distribution and the second distribution determined from the spin echo measurements from the first selected number of spin echo measurements have substantially equal logarithmic means and component amplitude sums, and the first distribution and the second distribution determined from the spin echo measurements from the second selected number of spin echo measurements have substantially equal logarithmic means and component amplitude sums.

84. The method of claim 81 further comprising estimating at least one petrophysical property from the stacked spin echo measurements from the second selected number of measurements.

85. The method of claim 81 wherein the at least one petrophysical property comprises at least one of porosity, free fluid volume and bound fluid volume.

86. The method of claim 71 wherein the first and second relaxation time distributions comprise transverse relaxation time.

* * * * *